United States Patent [19]

Scott et al.

[11] 3,976,595
[45] Aug. 24, 1976

[54] SULFONIC ACID-TYPE CATALYSTS USEFUL IN, FOR EXAMPLE, ESTERIFICATION REACTIONS

[75] Inventors: Robert H. Scott, Corpus Christi; Dan L. Gaulding, Driscoll, both of Tex.

[73] Assignee: Celanese Corporation, New York, N.Y.

[22] Filed: Mar. 17, 1975

[21] Appl. No.: 559,106

[52] U.S. Cl. .............................. 252/428; 252/426; 260/468 R; 260/486 R
[51] Int. Cl.² ........................................ B01J 27/02
[58] Field of Search ........................... 252/428, 426

[56] References Cited
UNITED STATES PATENTS

| | | | |
|---|---|---|---|
| 2,090,905 | 8/1937 | Stevens et al. | 252/428 X |
| 2,816,887 | 12/1957 | Lamborn | 252/428 X |
| 3,134,818 | 5/1964 | Farah et al. | 252/426 X |

*Primary Examiner*—Patrick P. Garvin
*Attorney, Agent, or Firm*—Ralph M. Pritchett

[57] ABSTRACT

Sulfonic acid catalysts useful in, for example, esterification reactions and which contain an admixture of any of several phosphorus compounds including specifically ortho-phosphoric acid are much less corrosive toward metal processing equipment than are sulfonic acid catalysts without the phosphoric admixture.

5 Claims, No Drawings

SULFONIC ACID-TYPE CATALYSTS USEFUL IN, FOR EXAMPLE, ESTERIFICATION REACTIONS

BACKGROUND OF THE INVENTION

Sulfonic acids, typically hydrocarbylsulfonic acids, are widely employed as acid-reacting catalysts, especially in esterification and hydrolysis reactions (which are, of course, simply the reverse of esterification). They have distinct advantages over strong mineral acids, some of which (sulfuric acid) can cause oxidation and/or discoloration of the esterification product while others (such as hydrochloric acid) are highly corrosive. Nitric acid is, of course, too highly reactive, while phosphoric acid, although not subject to some of the drawbacks just described, is relatively inactive as a catalyst and requires, for example, undesirably high reaction temperatures if a commercially-useful rate of reaction is to be obtained.

The sulfonic acid catalysts, which are free from many of the deficiencies of the mineral acids, are widely used in esterification reactions but still have the drawback of being quite corrosive toward process equipment, especially at the elevated temperatures employed in most esterifications. This not only results in the obvious reduction of equipment life but also, it has now been realized, causes unexpected problems with quality of the product of the esterification reaction in that, even though the rate of corrosion might not be excessive in some instances, the color of the product is adversely affected by very small quantities of corrosion products and/or organic products of decomposition catalyzed by these corrosion products.

Thus, there has been a continuing need for an esterification catalyst which would have the efficacy of the sulfonic acids (as exemplified by benzenesulfonic acid, methanesulfonic acid, and toluenesulfonic acid) without the accompanying drawback of high corrosivity.

It is an object of the present invention to provide a sulfonic acid-based acid-reacting catalyst which has the efficacy of the previously-used sulfonic acids but which is not so corrosive toward process equipment as such catalysts have been in the art as previously practiced. It is another object to provide a method for reducing the corrosivity of the process environment in processes in which a carboxylic acid is being esterified with a hydroxy compound in the presence of a sulfonic acid-type catalyst. Other objects will be apparent from the following detailed description and claims.

BRIEF SUMMARY OF THE INVENTION

In accordance with the present invention there is provided an improved sulfonic acid-type acid-reacting catalyst which consists essentially of at least one sulfonic acid, particularly a hydrocarbylsulfonic acid, in admixture with a least one phosphorus compound containing the radical

such mixtures having been discovered to be efficacious catalysts for use in, for example, esterification or hydrolysis reactions, while at the same time being much less corrosive than the sulfonic acids without the phosphorus compound admixture. The ordinary phosphoric acid of commerce, more specifically identified as ortho-phosphoric acid, is the preferred phosphorus compound inasmuch as it is entirely effective, low in cost, and readily available.

The invention also embraces within its scope an improved esterification process in which, in the carrying out of an esterification reaction with any of the sulfonic acid catalysts already known to the art, the corrosivity of the reactants is reduced by incorporating any of the phosphorus compounds as briefly identified above and as to be discussed more fully hereinbelow into the liquid mixture of carboxylic acid, hydroxy compound, and sulfonic acid which is contained in the esterification apparatus.

DETAILED DESCRIPTION OF THE INVENTION

Sulfonic acids broadly are applicable in the formulation of the present improved catalyst. That is, the organic component of the sulfonic acid molecule is not critical except that, of course, it should be free of constituents capable of reacting with the phosphorus compound. As a practical matter, however, hydrocarbylsulfonic acids are most readily available and will in actual fact be employed. By "hydrocarbyl" is meant alkyl, alkenyl, cycloalkyl, aryl, alkaryl, and aralkyl moieties. Specific examples which are of particular utility are the benzenesulfonic, methanesulfonic, and toluenesulfonic (specifically para-toluenesulfonic) acids which are in the present art widely employed as a esterification catalysts. Broadly speaking, however, any sulfonic acid which is useful as an esterification catalyst can be employed as a component of the present improved catalyst.

The phosphorus compounds applicable in formulating the catalyst are broadly those which contain the radical

These compounds include, for example, ortho-phosphoric and pyrophosphoric acids, phosphate salts such as the alkali metal phosphates including sodium phosphate, sodium hydrogen phosphate, amine phosphates such as the primary, secondary, tertiary, and quaternary methylamine salts, and organic phosphorus compounds such as diphenyl phosphite, triphenyl phosphite, and triphenylphosphine oxide. Phosphoric acid is preferred as being inexpensive, easy to handle, and containing a minimum of inert contaminants. By "phosphoric acid" is meant the substance ordinarily sold under this designation which comprises predominantly ortho-phosphoric acid but which also contains varying quantities of polymeric or oligomeric phosphorus acids. These acids are referred to broadly herein as "inorganic phosphorus acids", all being equally applicable as a genus of which ortho-phosphoric acid itself is a preferred species.

The improved catalyst consists essentially of a simple mixture of the sulfonic acid with the phosphorus compounds, which can be prepared by simply mixing the two materials. Alternatively, the phosphorus compounds, such as phosphoric acid, can be introduced into the liquid reaction medium (comprising carboxylic acid, hydroxy compound, product ester, and sulfonic acid catalyst) in an already-operating esterification reaction system when and as necessary to maintain in said liquid reaction medium at least some finite concentration of the phosphorus compound. This technique may be especially useful in many systems which operate over a long period of time inasmuch as there may be a small degree of continuous depletion of the phosphorus compound from the system as a result of, for example, the formation of films on the surfaces of the metal apparatus. This is a pertinent consideration because the phosphorus compound is effective in extremely small concentrations, so that it is never necessary (although it is not harmful) to have in the catalyst mixture more than a very small proportion of the phosphorus compound as compared with the sulfonic acid. Extremely small proportions of the phosphorus compound, if continuously maintained in the reaction medium in this manner, can make the sulfonic acid much less corrosive than when none of the phosphorus compound at all is present.

Although, as just explained, the beneficial results are appreciable even when trace quantities of the phosphorus compound are present, it is recommended that the phosphorus compound be present in the catalyst mixture in a concentration of at least about 1% by weight, calculated on the basis of the total amount of sulfonic acid and phosphorus compound present in the mixture, the phosphorus compound being computed as orthophosphoric acid. Broadly, it is recommended that the amount of phosphorus compound present, computed on this same basis, be from about 0.5% to about 50% of the mixture of phosphorus compound and sulfonic acid. Proportions greater than about 50% are not deleterious, but are not necessary. More preferably, it is recommended that the phosphorus compound be an inorganic phosphorus acid and that it be present in the catalyst in a concentration of at least about one part by weight per 100 parts of the sulfonic acid, with excellent results having specifically been obtained with a catalyst mixture containing about 3% of phosphoric acid in a sulfonic acid which is a member of the group consisting of methanesulfonic acid, toluenesulfonic acid, and benzenesulfonic acid.

With further respect to the foregoing, it will be understood that inert diluents can be present in the improved catalyst if desired, as, for example, for the purpose of increasing the volume of the catalyst to improve the accuracy of metering in a continuously-operating reaction system.

The effective concentration of the catalyst in an esterification reaction system is the same (computed on the basis of the sulfonic acid content) as already known to the esterification art. This is not critical, since the present catalyst has the same effectiveness, per unit content of sulfonic acid, as the sulfonic acid catalyst already known to the art. A typical useful concentration, however, is about 3% by weight of the sulfonic acid in a typical liquid phase esterification reaction. In any case, and regardless of the ratio of phosphorus compound to sulfonic acid employed in formulating the present improved mixed catalyst, it is recommended that the concentration of phosphorus compound in the liquid phase reactants contained in the esterification apparatus be at least about 0.0005% by weight (5.0ppm) computed as orthophosphoric acid. Preferably, the concentration of the phosphorus compound, computed on the same basis, should be at least about 0.02 weight percent. A concentration greater than about 1%, computed on the same basis, is not necessary.

The present improved catalyst is effective even at elevated temperatures, e.g., temperatures of the order of about 200°C and it has been found to be quite effective at 110°C. Even at higher temperatures, some improvement obtains in using the present improved catalyst as compared with a sulfonic acid alone, with temperature thus not being a controlling factor in application of the catalyst. That is, in any temperature regime within which a sulfonic acid alone can be employed at all, the incorporation of a phosphorus compound of the type described herein will reduce the corrosion rate.

It is to be noted that water, which is sometimes present in small quantities in esterification reaction batches, normally has the effect of accelerating corrosion. In many systems, for example, the corrosivity of the reactant containing acidic catalysts such as the sulfonic acids is appreciably greater when water concentration is greater than about 2 weight percent as compared with lower water concentrations. Here again, however, as in the matter of temperature discussed hereinabove, the present catalyst containing the phosphorus compound additive is, at a given level of water concentration, less corrosive than the sulfonic acids used alone under the same conditions. Incorporation of the phosphorus compound, in fact, can in some cases of relatively high water concentration reduce the corrosion rate to a manageable level whereas with the sulfonic acids alone the corrosion rate is so high as to be a serious obstacle to successful commercial operation.

The following example is given to illustrate the invention further. It will be understood that many variations can be made therefrom within the scope of the invention.

EXAMPLE

In the following example corrosion rates (expressed in thousands of an inch per year, abbreviated mpy) were determined by use of an electrical resistance-type corrosion probe. The essential element of such a probe is an electrical resistance of known cross-section and length formed from a metal the corrodibility of which is to be tested. An electrical current is continuously passed through this metal element at a controlled rate and under a controlled voltage so that it is possible to measure continuously the increase in required voltage (or the decrease in electrical current under conditions of constant voltage) as the continuing corrosion of the metal reduces the cross-section of the element with resulting increase in electrical resistance. This is directly translatable, by methods not pertinent to the present discussion, into corrosion rate of the metal.

The following tests were carried out on the residue stream drawn from the base of a continuously-operating still-reactor column within which n-butanol and acrylic acid were being reacted in the presence of para-toluenesulfonic acid catalyst to form butyl acrylate. Acrylic acid and n-butanol were continuously introduced into the base section of the column, where they were mixed into a continuously-circulating stream drawn from the base of the column which then passed through a reboiler and was reintroduced into the column below the first tray. The esterification reaction took place in the base of the column, from which there was a small continuous drawoff of refractory tars.

The overhead vapors from the still-reactor column, comprising butyl acrylate, unreacted butanol, water of reaction, and low-boiling by-products, was condensed and passed into a phase-separation vessel, within which it separated into an aqueous phase and a water-immiscible organic phase. A portion of each of these two liquid phases was returned to the head of the column as reflux, while a portion of each phase was also withdrawn for subsequent workup. The withdrawn organic phase was redistilled, in a sequence the details of which are not pertinent to the present invention, to recover the final purified butyl acrylate product. The withdrawn portion of the aqueous phase was distilled to recover the water for process re-use and also to work up the dissolved organic components for recovery and/or further disposition by methods which are also outside the scope of the present invention.

The liquid contained in the base of the reaction column, i.e., the liquid reaction phase in which the esterification was taking place, and contained, by weight, approximately 8% n-butanol, 23% acrylic acid, 35% n-butyl acrylate, 3% para-toluenesulfonic acid, 2.5% water, 16% oligomeric high-boiling acrylate esters, and 7% polyacrylic acid.

By continuously passing a portion of the above-described residue reaction product through a cell containing an electrical resistance corrosion probe as described above, it was determined that the corrosion rate of Type 316 stainless steel at 105°C was 85 mpy.

Incorporation of 1.0% commericial phosphoric acid (i.e., predominantly ortho-phosphoric acid) into the liquid reaction medium before passing it over the corrosion probe resulted in a rapid drop in corrosion rate until, after about 8 hours, the corrosion rate had stabilized at 35 mpy.

Polyphosphoric acid (a commercial mixture of polyphosphoric acids), at the same concentration at which the ortho-phosphoric acid had been employed, gave substantially the same results in reducing corrosion rate. Substantially the same beneficial results were also obtained with tri n-butyl phosphate. These compounds were all much more effective than triphenylphosphine oxide.

Optimum results were, in general, obtained with the group of inhibitors consisting of the inorganic phosphorus acids, tri-hydrocarbyl phosphate esters, and phosphate salts of non-varivalent metals. The inorganic phosphorus acids are especially preferred.

In addition to the obvious benefit of reducing corrosion rate and so increasing process equipment life which is obvious from the foregoing test results, an additional, and unexpected, benefit was also realized. Fouling of high-temperature heat transfer surfaces in the residue circuit of the above-described still-reactor had been very heavy. After introduction of the phosphorus compounds as inhibitors into the reaction system, the degree of fouling was sharply reduced. Examination of some of the foulant deposits indicated that they comprised toluenesulfonic acid salts of iron and nickel, presumably formed by reaction of the esterification catalyst with the stainless steel of which the still-reactor was fabricated. The reduction in corrosivity due to introduction of the phosphorus inhibitors was sufficient to bring about a marked amelioration of the fouling problem.

The embodiments of the invention in which an exclusive property or privilege is claimed are defined as follows:

1. An improved acid-reacting catalyst consisting essentially of a mixture of at least one hydrocarbonyl sulfonic acid with at least one phosphorus compound selected from the group consisting of tri-hydrocarbyl phosphate esters, phosphate salts of alkali metals, and the inorganic phosphorus acids.

2. The catalyst of claim 1 wherein the hydrocarbylsulfonic acid constitutes at least about 50% of the mixture by weight.

3. The catalyst of claim 2 wherein the phosphorus compound is present in the mixture in a concentration of from about 1.5% to about 50% of the mixture by weight, computed as orthophosphoric acid.

4. The catalyst of claim 3 wherein the phosphorus compound is an inorganic phosphorus acid in a concentration of at least about one part be weight per 100 parts of hydrocarbylsulfonic acid.

5. The catalyst of claim 4 wherein the phosphorus acid is orthophosphoric acid.

* * * * *